United States Patent
Fischell et al.

[11] Patent Number: 5,324,262
[45] Date of Patent: Jun. 28, 1994

[54] INTRODUCER SHEATH WITH EXPANDABLE OUTER TUBE AND METHOD OF USE

[75] Inventors: Robert E. Fischell, Dayton, Md.; Tim A. Fischell, Nashville, Tenn.

[73] Assignee: Cathco, Inc., Dayton, Md.

[21] Appl. No.: 15,530

[22] Filed: Feb. 9, 1993

[51] Int. Cl.5 ............... A61M 29/00; A61M 31/00; A61M 29/02
[52] U.S. Cl. ............................ 604/96; 606/192; 604/53
[58] Field of Search ............ 604/53, 55, 96–103, 604/104, 164, 167, 174, 175, 264, 278, 280, 283; 606/192–198

[56] References Cited
U.S. PATENT DOCUMENTS

| | | | |
|---|---|---|---|
| 4,207,899 | 6/1980 | Patel | 604/103 X |
| 4,222,384 | 9/1980 | Birtwell | 604/103 |
| 4,249,535 | 2/1981 | Hargest, III | 604/265 X |
| 4,335,723 | 6/1982 | Patel | 604/103 X |
| 4,751,924 | 6/1988 | Hammerschmidt et al. | 128/207.15 |
| 4,846,812 | 7/1989 | Walker et al. | 604/264 |
| 4,884,573 | 12/1989 | Wijay et al. | 606/194 |
| 4,950,257 | 8/1990 | Hibbs et al. | 604/265 |
| 4,955,890 | 9/1990 | Yamamoto et al. | 606/108 |
| 5,180,376 | 1/1993 | Fischell | 604/282 |
| 5,269,770 | 12/1993 | Conway et al. | 604/265 |

Primary Examiner—John D. Yasko
Assistant Examiner—Adam J. Cermak
Attorney, Agent, or Firm—Morton J. Rosenberg; David I. Klein

[57] ABSTRACT

An introducer sheath (10) is provided for percutaneous insertion of catheters into a blood vessel. The introduction of the sheath (10) through a wall of blood vessel causes an opening to be formed through which blood may pass from the blood vessel. The sheath(10) includes an inflatable collar (20) which may be expanded under pressurized inflation of fluid inserted within the inflatable collar (20) to expand into contiguous contact with a periphery of the opening formed by the sheath (10) to prevent blood leakage through the blood vessel wall opening.

7 Claims, 3 Drawing Sheets

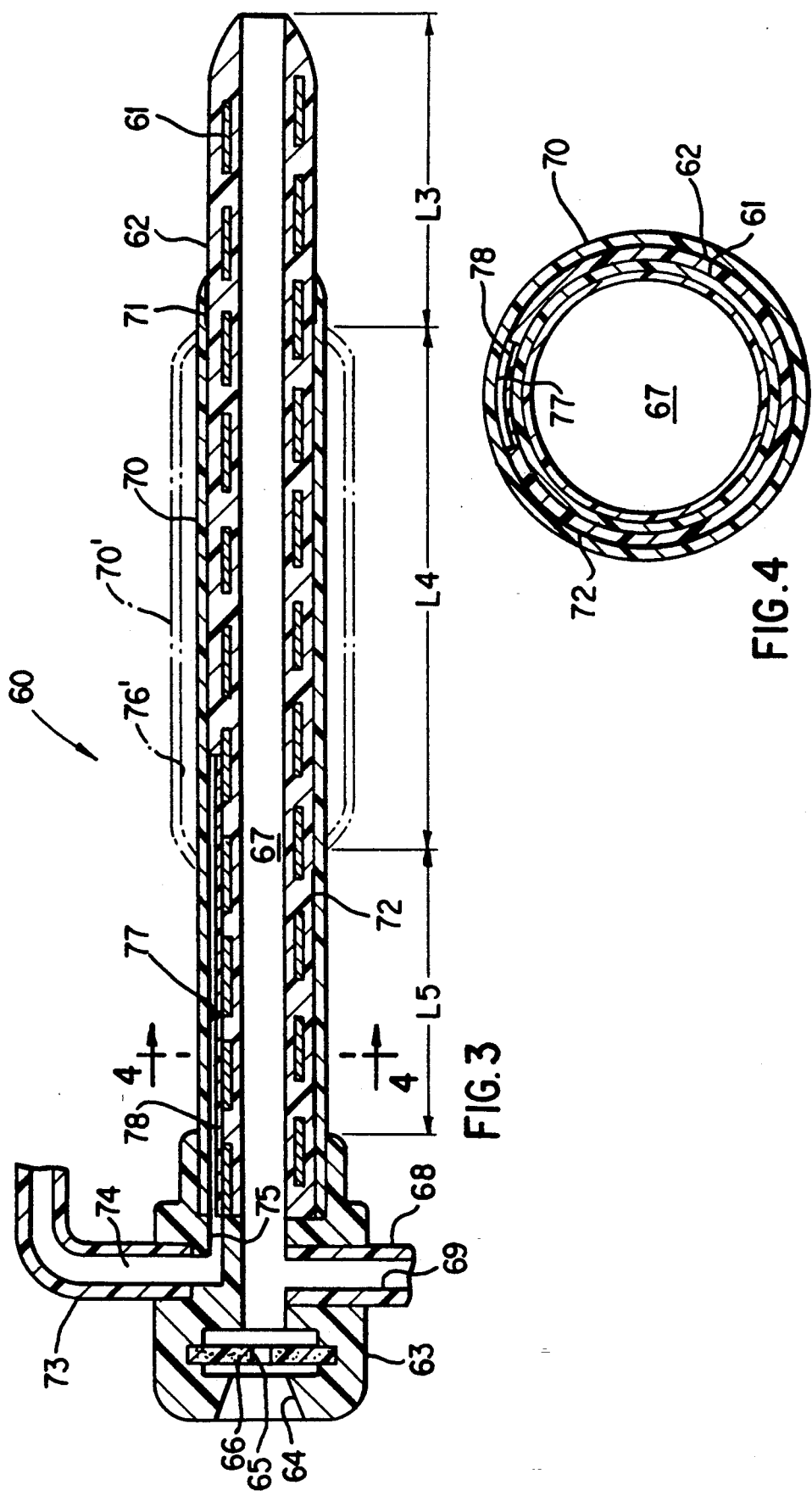

5,324,262

INTRODUCER SHEATH WITH EXPANDABLE OUTER TUBE AND METHOD OF USE

FIELD OF USE

This invention is in the field of percutaneously inserted introducer sheaths that allow passage of guide wires and/or catheters into blood vessels.

BACKGROUND OF THE INVENTION

Introducer sheaths are used in interventional procedures to percutaneously insert guide wires and/or catheters into blood vessels. These sheaths are frequently inserted percutaneously into the femoral artery at the groin in order to perform angioplasty or atherectomy of coronary arteries. After a coronary procedure, the sheath is left in place for at least several hours so that rapid treatment of a post-procedure complication can be readily accomplished. One frequent complication which occurs with this procedure is bleeding around the sheath where it penetrates through the arterial wall. Treatment occasionally requires replacing the sheath with another sheath having a larger outer diameter. This procedure requires a physician and is fairly involved and time consuming.

Another problem occurs when a sheath is inserted through a highly curved iliac artery. The iliac artery can be so tortuous that, even if the sheath does not kink, the sheath bends so sharply that the passage of a guiding or angioplasty catheter is precluded or at least made very difficult.

SUMMARY OF THE INVENTION

The present invention is an introducer sheath with an expandable outer tube which is designed to overcome the shortcomings of existing introducer sheath devices. Specifically, one embodiment of the present invention has an expandable outer tube located at a proximal section of the sheath. Thus, when bleeding occurs around the sheath where it penetrates the arterial wall, instead of replacing the sheath with a sheath having a larger outside diameter, one merely inflates the outer tube to obtain the desired increase in the sheath's outer diameter. This can be done by a nurse or a technician. Thus the bleeding can be stopped without sheath replacement and without requiring the services of a physician.

Another embodiment of this invention utilizes a sheath which tapers in the proximal direction to a larger outside diameter. Thus, bleeding can be stopped by advancing the sheath in the distal direction until the outside diameter at the point of entry through the arterial wall is large enough to stop the bleeding.

Another use for an introducer sheath with an expandable outer tube is to straighten a tortuos iliac artery. In this embodiment, the sheath has an expandable, inflatable outer tube whose distal end lies approximately one inch from the sheath's distal end and whose proximal end lies approximately 3 inches from the sheath's proximal end. This mid-section tube is inflatable to a pressure as high as 2000 psi using a fluid injected from a said arm located in a proximal fitting of the sheath. When this mid-section inflatable tube expands to a larger outer diameter because of the injection of a high pressure fluid such as contrast medium or saline, any tortous blood vessel in which that sheath is placed will tend to be straightened.

Thus, an object of thus invention is to provide an introducer sheath having an outer tube that can be expanded after insertion of the sheath into a blood vessel.

Another object is to have only a proximal; i.e., collar section, of the sheath expandable so as to stop bleeding that can occur around the sheath where it passes through the arterial wall.

Still another object of this invention is to have a sheath with a collar that is tapered to a larger diameter in the proximal direction which collar can stop bleeding by advancing the sheath in the distal direction.

Still another object of this invention is to have an inflatable, expandable tube at the sheath's mid-section which, when pressurized with fluid, can cause straightening of a highly curved blood vessel.

These and other objects and advantages of this invention will become obvious to persons of ordinary skill in this art upon reading of the detailed description of the invention presented herein in conjunction with the related drawings.

BRIEF DESCRIPTION OF THE DRAWINGS

FIG. 3 is longitudinal cross section of an introducer sheath having an expandable outer tube located at the sheath's mid-section.

FIG. 4 is a transverse cross section of the sheath at section 4—4 of FIG. 3.

DETAILED DESCRIPTION OF THE DRAWINGS

Figure 1:
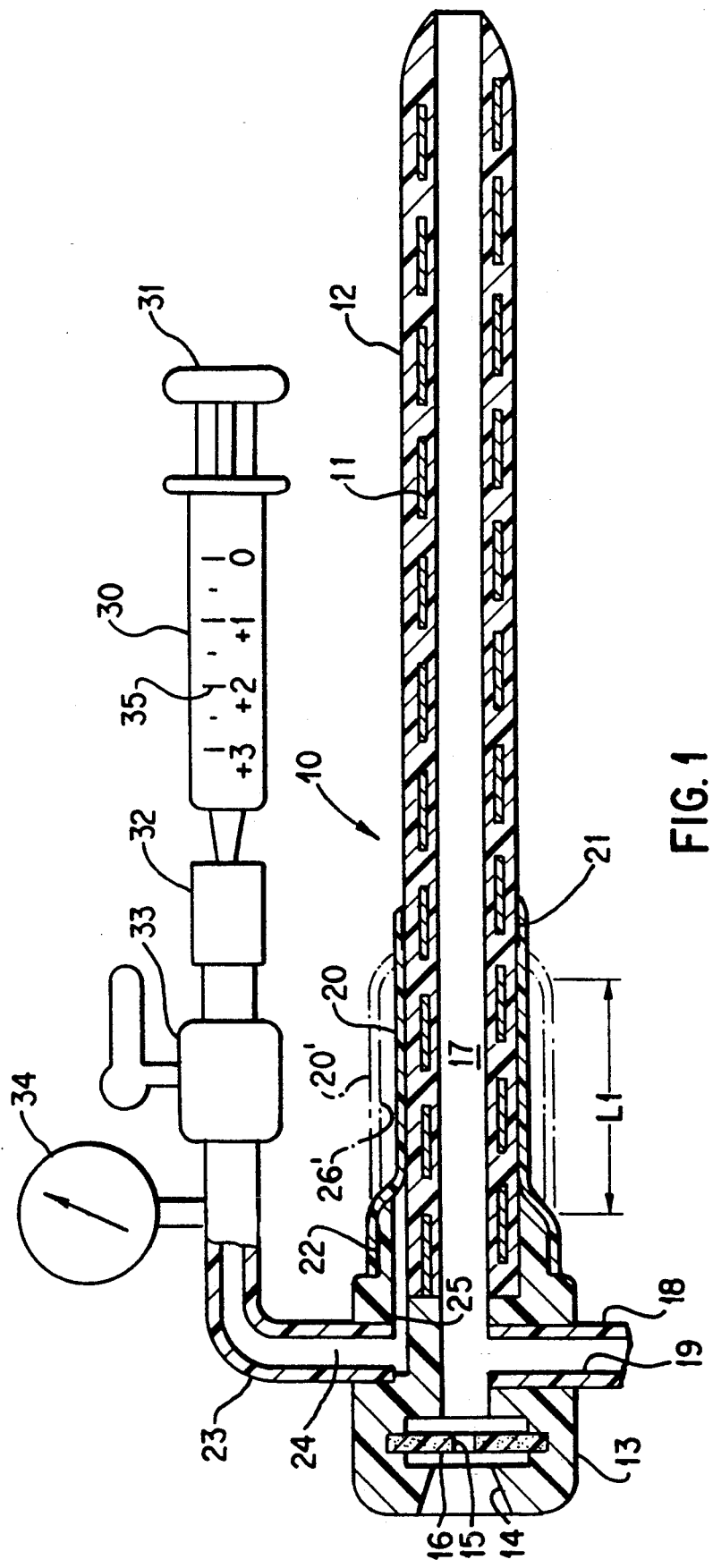
FIG. 1 is a longitudinal cross-section of an introducer sheath having an expandable outer tube situated at a proximal section of the sheath.

FIG. 1 illustrates an expandable (i.e., inflatable) collar 20 located at a proximal section of the sheath 10. The sheath 10 has a flat wire helical coil 11 encapsulated in a plastic body 12, a proximal fitting 13 having a tapered inlet port lumen 14 which leads to an opening 15 in a hemostasis valve 16. The basic structure of such a sheath 10 having a flat wire helical coil 11 is described in U.S. patent application Ser. No. 07/965,961 filed by the present inventors on Nov. 3, 1992, which Patent Application is included herein by reference. The opening 15 leads to the sheath's central lumen 17. A side arm 18 which typically terminates in a Luer fitting (not shown) has a lumen 19 that joins the lumen 17 of the body 12 of the sheath 10. The distal end of the expendable collar 20 is joined to the outer surface of the body 12 by an adhesive joint 21. The proximal end of the expandable collar 20 is joined by an adhesive joint 22 to the distal end of the fitting 13. Dotted lines indicate the position of the collar 20' forming the chamber 26' when inflated by a pressurized fluid. The liquid or gas fluid would come from a syringe 30 having a plunger 31. The fluid would flow through a Luer lock fitting 32 which typically is part of a stopcock 33 then through the lumen 24 of the side arm 23 of the proximal fitting 13. The lumen 24 joins to the lumen 25 which fills the chamber 26' of the expanded collar 20'. The length L1 of the collar 20 would typically be between 1 and 3 inches and certainly less than 6 inches. The inside diameter of the sheath 10 would typically be between 0.050 and 0.25 inches. The flat wire coil 11 would typically be made from type 304 stainless steel, the body 12 and collar 20 would be made from an elastomer such as polyurethane, polyethylene, PVC, Surlyn, silicone rubber, latex rubber, or an equivalent plastic material.

It should be understood that for the purpose of clarity the radial dimensions of FIG. 1 are exaggerated; i.e., the radial dimensions are too large compared to the longitudinal dimensions. Thus, the total wall thickness of the body 12 is between 0.005 and 0.015 inches and the length of the sheath 10 is typically between 5 and 30 inches.

In use, the sheath 10 would typically be percutaneously inserted into the femoral artery at the groin. If bleeding occurs around the sheath 10 where it penetrates through the arterial wall, the syringe 30 typically containing a contrast medium or saline solution would inject that fluid through the Luer lock fitting 31 through the (open) two-port stopcock 33 and then through the side arm 23 into the collar chamber 26'. An indicator scale 35 on the syringe 30 would indicate to the operator the increase in diameter of the collar 20 corresponding to the position of the distal end of the plunger 31 relative to an indicator mark on the scale 35. For example, a diameter increase for the collar 20 of the French size (0.013 inches) would be marked +1 on the indicator scale 35. Typically the outside diameter of the collar 20 could be increased by as much as three French sizes which would be adequate to stop blood leakage around the sheath 10 where it penetrates through the arterial wall. A pressure gauge 34 could also be used to provide quantification of the increase of the outer diameter of the collar 20.

Figure 2:
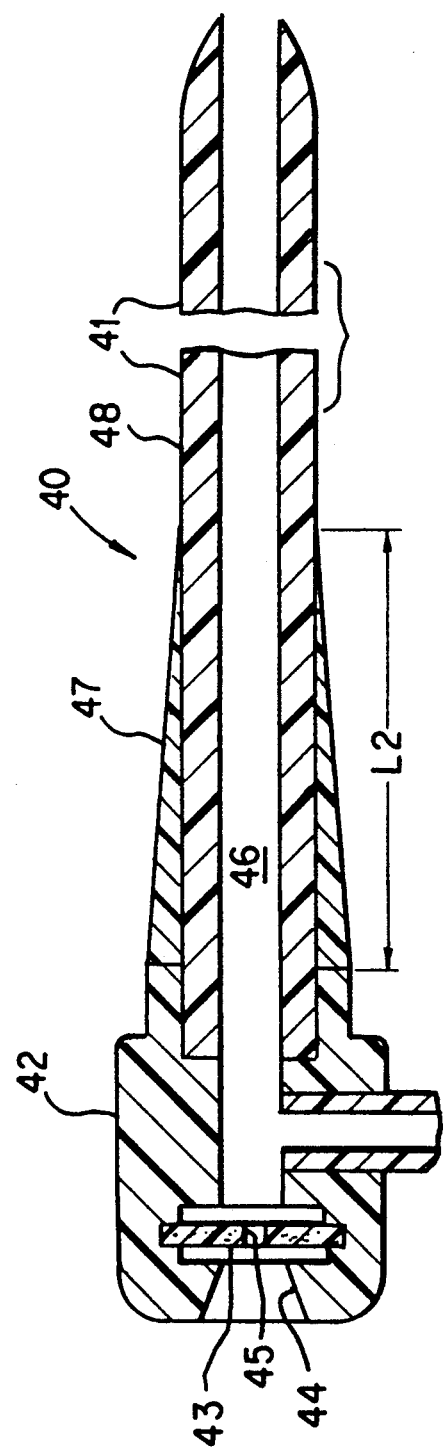
FIG. 2 is a longitudinal cross section of an introducer sheath having a tapered cone located at a proximal section of the sheath.

FIG. 2 illustrates a sheath 40 having a body 41, a proximal fitting 42 with a tapered entry lumen 44 which joins the opening 45 in a hemostasis valve 43; the opening 45 joining to the lumen 46 of the body 41. This tapered collar design is equivalent in function to expanding the diameter of the sheath 40 in the proximal direction. Thus, the sheath 40 would be advanced through the femoral artery until the end point 48 lies outside of the arterial wall. Then if bleeding occurs subsequent to sheath insertion, the sheath 40 would be advanced in the distal direction until the increased outer diameter of the tapered collar 47 causes the bleeding to stop. The sheath 40 would typically have an elastomer body from a plastic material such as polyurethane or Teflon, and the tapered collar 47 would typically be formed out of the same or a similar plastic material. The length L2 of the collar 47 would typically be 1 to 6 inches.

FIG. 3 illustrates a sheath 60 having a flay wire helical coil 61 encapsulated in a plastic body 62. The coil 61 and the body 62 are joined at their proximal end to a proximal fitting 63 having a tapered entry lumen 64 which leads into the opening 65 of the hemostasis valve 66 and then into the sheath's central lumen 67. A mid-section inflatable, expandable tube 70 assumes the shape shown in the dotted lines as the tube 70' when filled with a high pressure fluid such as contrast medium. The fluid would flow through the side arm 73 having a lumen 74 which joins the lumen 75 which continues into the lumen 77 that joins the chamber 76'.

FIGS. 3 and 4 show the wire coil 61, plastic body 62 and the lumen 77 which is cut into the body 12. An extremely thin plastic liner 78 can be placed at the bottom of the lumen 77 to prevent fluid from passing through the spaces between the turns of the wire coil 61.

The length L3 from the sheath's distal end to the distal adhesive joint 71 at the expandable tube's distal end 0.5 to 3 inches. As seen in FIG. 4, the proximal adhesive joint 72 extends completely around the circumference of the body 62 except for the arc subtended by the lumen 77. The joint 72 prevents expansion of the tube 70 in the collar region of the sheath 60; i.e., from the proximal fitting 63 for the distance L5 beyond the distal end of the fitting 63. The length L5 of the joint 72 is between 1 and 6 inches. The mid-section expandable tube 70 would be continuously expandable over a length L4 between 4 and 15 inches. In the same manner as provided in the embodiment shown in FIG. 1, a side arm 68 which typically terminates in a Luer fitting (not shown) has a lumen 69 that joins the lumen 67 of the body 62 of the sheath 60.

The material and fluids used and means for setting the increased outer diameter of the tube 70 would be equivalent to the embodiment shown of FIG. 1. Except for the unique structure associated with the mid-section expandable tube 70, the dimensions of the sheath 60 would be the same as those for the sheath 10 of FIG. 1. The wall thickness of the tube 70 would be typically be between 0.002 and 0.010 inches. Higher pressures would typically be used for the mid-section tube 70 as compared to the collar tube 20. In both embodiments, the flat wire helical coils 11 or 61 would resist inward deflection from the pressurized fluid, which deflection could trap a guiding catheter.

It is also envisioned that the expandable outer tube could be placed directly over the flat wire helical coil without any intervening outer portion of the body 12 of FIG. 1 or the body 62 of FIG. 3.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An introducer sheath for percutaneous insertion of catheters into a blood vessel comprising:
    an elongated, hollow, generally cylindrical body having proximal and distal ends;
    a proximal fitting having a lumen formed therein, said proximal fitting being secured to said proximal end of said cylindrical body;
    a hemostasis valve mounted within said proximal fitting; and,
    means for preventing blood leakage through an opening formed through a wall of said blood vessel by said introducer sheath, said blood leakage prevention means including an outer inflatable expandable tube mounted on the cylindrical body, said inflatable tube being inflatable into contiguous contact with a periphery of said opening, said tube being inflated by means of a pressurized inflation fluid which enters an interior chamber of the inflatable expandable tube through said lumen of the proximal fitting, the expandable tube being joined at its proximal end to the proximal fitting's distal end.

2. The sheath of claim 1 wherein the expandable tube has an expandable section which is located at a proximal section of the sheath.

3. The sheath of claim 2 wherein the expandable tube is less than 6 inches long.

4. The sheath of claim 2 wherein the expandable tube is less than 3 inches long.

5. A method for stopping the bleeding from around a sheath inserted through the wall of an artery comprising the following steps:

percutaneously advancing an introducer sheath until the sheath's distal end lies within an arterial lumen; and, inflating an outer tube collar located at a proximal section of the sheath so as to enlarge the sheath's outer diameter to a diameter substantially equal to a diameter of an opening formed in said wall of said artery by said introducer sheath.

6. The method of claim 5 further including the step of using a fluid filled syringe with indicator marks to set the extent to which the outer diameter of the outer tube is expanded.

7. The method of claim 5 further including the step of using a pressure gauge to set the extent to which the outer diameter of the outer tube is expanded.

* * * * *